US012673105B2

(12) United States Patent (10) Patent No.: US 12,673,105 B2
Castro et al. (45) Date of Patent: Jul. 7, 2026

(54) MULTI-FUNCTIONAL CANCER DRUG DELIVERY NANODEVICE FOR PRECISION MEDICINE

(71) Applicant: Ohio State Innovation Foundation, Columbus, OH (US)

(72) Inventors: Carlos Castro, Columbus, OH (US); Christopher Lucas, Columbus, OH (US); Patrick Halley, Columbus, OH (US); John Byrd, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 864 days.

(21) Appl. No.: 17/046,521

(22) PCT Filed: Apr. 9, 2019

(86) PCT No.: PCT/US2019/026535
§ 371 (c)(1),
(2) Date: Oct. 9, 2020

(87) PCT Pub. No.: WO2019/199787
PCT Pub. Date: Oct. 17, 2019

(65) Prior Publication Data
US 2021/0162065 A1 Jun. 3, 2021

Related U.S. Application Data

(60) Provisional application No. 62/751,991, filed on Oct. 29, 2018, provisional application No. 62/655,500, filed on Apr. 10, 2018.

(51) Int. Cl.
| | |
|---|---|
| *A61K 47/69* | (2017.01) |
| *A61K 31/704* | (2006.01) |
| *A61K 39/395* | (2006.01) |
| *A61K 47/10* | (2017.01) |
| *A61K 47/26* | (2006.01) |
| *A61K 47/54* | (2017.01) |
| *A61K 47/68* | (2017.01) |
| *A61P 35/00* | (2006.01) |
| *C12N 15/113* | (2010.01) |
| *A61K 39/00* | (2006.01) |

(52) U.S. Cl.
CPC .......... *A61K 47/549* (2017.08); *A61K 31/704* (2013.01); *A61K 39/39558* (2013.01); *A61K 47/10* (2013.01); *A61K 47/26* (2013.01); *A61K 47/6921* (2017.08); *A61P 35/00* (2018.01); *C12N 15/113* (2013.01); *A61K 2039/505* (2013.01); *A61K 2039/51* (2013.01); *C12N 2310/11* (2013.01); *C12N 2310/14* (2013.01); *C12N 2310/141* (2013.01)

(58) Field of Classification Search
CPC .. A61K 47/68; A61K 47/10; A61K 2039/505; A61K 2039/51; A61K 47/60; C12N 15/113
See application file for complete search history.

(56) References Cited

U.S. PATENT DOCUMENTS

| | | | |
|---|---|---|---|
| 9,765,341 B2 | 9/2017 | Bachelet et al. | |
| 11,410,746 B2 * | 8/2022 | Veneziano ............. | G16B 15/00 |
| 2008/0177053 A1 | 7/2008 | Matsuura et al. | |

FOREIGN PATENT DOCUMENTS

| | | |
|---|---|---|
| WO | 2012061719 A2 | 5/2012 |
| WO | 2013030831 A2 | 3/2013 |
| WO | 2017127033 A1 | 7/2017 |
| WO | 2017189870 A1 | 11/2017 |

OTHER PUBLICATIONS

Overdijk et al., mAbs, 7:2, 2015, 311-320.*
Walsh et al., Molecular Pharmaceutics, 3/6, 2006, 644-653.*
Halley, DNA Origami as a Drug Delivery Vehicle for in vitro and in vivo Applications, Master's Thesis, 2016.*
EP Search Report, EP Patent App. 19784893.0, mailed Apr. 4, 2022 (14 pages).
Smith, David, et al., "Nucleic acid nanostructures for biomedical applications," Nanomedicine, vol. 8, No. 1 (2013), pp. 105-121.
Hong, Fan, et al., "DNA Origami: Scaffolds for Creating Higher Order Structures," Chem. Rev., vol. 117 (2017), pp. 12584-12640.
Qin, Weiwei, et al., "Nanomaterials in Targting Cancer Stem Cells for Cancer Therapy," Frontiers in Pharmacology, vol. 8 (2017) (15 pages).
Jiang, Dawei, et al., "DNA nanomaterials for preclinical imaging and drug delivery," Journal of Controlled Release, vol. 239 (2016), pp. 27-38.
International Search Report issued for PCT/US2019/026535, mailed Jun. 20, 2019.
Halley et al., Daunorubicin-Loaded DNA Origami Nanostructures Circumvent Drug Resistance Mechanisms in a Leukemia Model, Small, vol. 12, No. 3, p. 308-320, 2016.
Kearney et al., DNA Origami: Folded DNA-Nanodevices That Can Direct and Interpret Cell Behavior, Advanced Materials, vol. 28, Iss. 27, pp. 5509-5524, 2016.

(Continued)

*Primary Examiner* — Kyle A Purdy

(74) *Attorney, Agent, or Firm* — Pabst Patent Group LLP

(57) ABSTRACT

Disclosed herein are DNA origami nanostmcture that can be functionalized for personalized and targeted drug delivery. The disclosed nanostructures enter cells through the endo-lysosomal pathway and circumvent drug resistance mecha-nisms in target cells. The disclosed nanostructures can be loaded small molecule drugs (e.g. anthracyclines, anti-me-tabolites) and nucleic acids (e.g. antisense oligonucleotides, siRNA, miRNA) with targeting and/or therapeutic antibod-ies against tumor-specific antigens (e.g. anti-CD33, anti-CD20) that can be modified to treat to a wide range of cancers and ultimately tailored to specific patients' needs for precision medicine.

14 Claims, 11 Drawing Sheets

(56) References Cited

OTHER PUBLICATIONS

Ponnuswamy et al., Oligolysine-based coating protects DNA nanostructures from low-salt denaturation and nuclease degradation, Nature Communications, p. 1-9, 2017.

Bastings, Maartje M. C., et al., "Modulation of the Cellular Uptake of DNA Origami through Control over Mass and Shape," Nano Letters, vol. 18 (2018), pp. 3557-3564.

Zhao, Yong-Xing, et al., "DNA Origami Delivery System for Cancer Therapy with Tunable Release Properties," ACS Nano, vol. 6, No. 10 (2012), pp. 8684-8691.

Jiang, Qiao, et al., "DNA Origami as a Carrier for Circumvention of Drug Resistance," J. Am. Chem. Soc., vol. 134 (2012), pp. 13396-13403.

* cited by examiner

= therapeutic oligo (siRNA or miRs)

= Targeting Ab

= intercalating drug

= polyetheleneglycol conjugated oligo

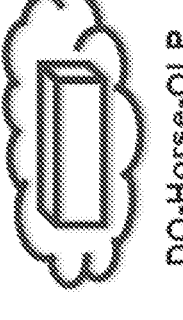

DO-Horse-PEG

- 65 PEGylated oligos attached to DO by complementary oligos embedded in DO
- incomplete PEG coverage
- attachment oligos subjected to nuclease degradation

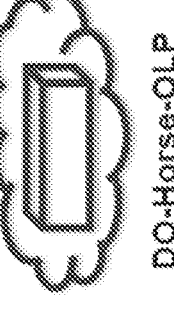

DO-Horse-OLP

- 10 Lys attached to PEG molecule
- electrostatic interactions (10 Lys to anionic DNA backbone)
- 'shell' of PEG around each exposed helix
- ~1,450 PEG molecules per DO structure
- literature support for improving PK

FIG. 7

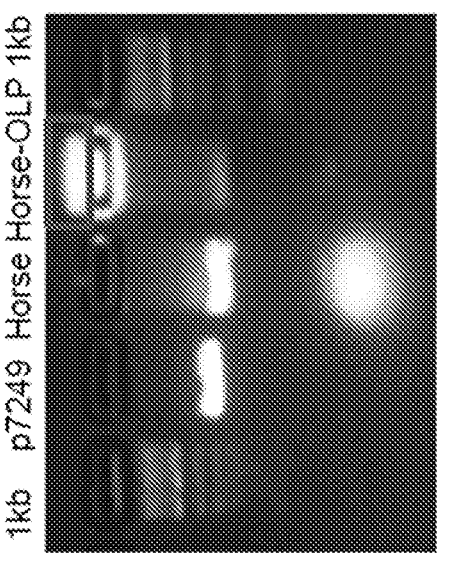
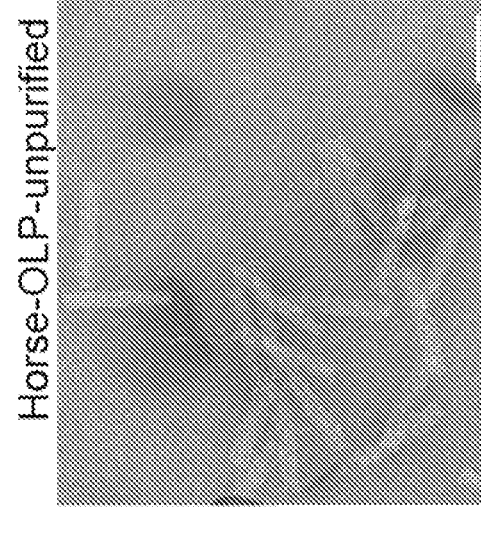
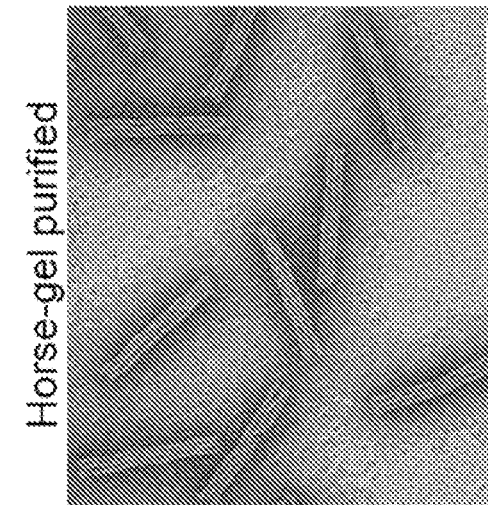
FIG. 8

MULTI-FUNCTIONAL CANCER DRUG DELIVERY NANODEVICE FOR PRECISION MEDICINE

CROSS-REFERENCE TO RELATED APPLICATIONS

This application is a National Stage of International Application No. PCT/US2019/026535, filed Apr. 9, 2019, which claims benefit of U.S. Provisional Application No. 62/655,500, filed Apr. 10, 2018, and Application Ser. No. 62/751,991, filed Oct. 29,2018, which are hereby incorporated herein by reference in their entireties.

STATEMENT REGARDING FEDERALLY SPONSORED RESEARCH OR DEVELOPMENT

This invention was made with Government Support under Grant No. CA140158 CA197734, and CA009338 awarded by the National Institutes of Health. The Government has certain rights in the invention.

BACKGROUND

Anthracyclines (doxorubicin, daunorubicin, and idarubicin) are very effective chemotherapeutic drugs to treat many cancers; however, the development of multiple drug resistance (MDR) is one of the major limitations for their clinical applications. The development of MDR to chemotherapy remains a major challenge in the treatment of cancer. Nanoparticle (NP) delivery systems have been shown to be promising carriers to improve the therapeutic effect of anthracyclines mainly due to the enhanced permeability and retention (EPR) effect in solid tumors, while they minimize systemic exposure, enhance drug efficacy and reduce non-specific toxicity. Doxil, a DOX-encapsulated polyethylene glycol (PEG)-coated liposome formulation with the particle size of ~100 nm, was approved in 1995 for the treatment of ovarian cancer, AIDS-related Kaposi's sarcoma, and multiple myeloma. The DOX PEGylated liposomes demonstrate slower plasma clearance rate, prolonged circulation time in blood, and decreased volume of distribution than either traditional DOX liposomes or free DOX. However, this liposome formulation has not addressed MDR which continues to be a major hurdle in cancer therapy. Nano-delivery systems need to be developed that can effectively overcome MDR.

SUMMARY

Scaffolded DNA origami nanotechnology allows for the generation of pre-defined shaped nanoscale objects via molecular self-assembly as well as a robust platform for drug delivery applications. DNA origami nanostructures can be functionalized with targeting moieties and effectively loaded with anthracyclines (e.g. doxorubicin and daunorubicin) and thrombin. Furthermore, drug-loaded DNA origami nanostructures induce an enhanced anti-cancer effect relative to free drug in both solid tumor and hematologic model systems in vitro, while thrombin-loaded nanostructures induce tumor necrosis and inhibit tumor growth in vivo in a targeted manner. Despite this exciting promise, the toxicology, immunogenicity, bio-distribution, and pharmacokinetics of DNA origami nanostructures in vivo remain ill defined.

Disclosed herein are DNA origami nanostructure that can be functionalized for personalized and targeted drug delivery. The disclosed nanostructures enter cells through the endolysosomal pathway and circumvent drug resistance mechanisms in target cells.

The disclosed nanostructures can be loaded small molecule drugs (e.g. anthracyclines, anti-metabolites) and nucleic acids (e.g. antisense oligonucleotides, siRNA, miRNA) with targeting and/or therapeutic antibodies against tumor-specific antigens (e.g. anti-CD33, anti-CD20) that can be modified to treat to a wide range of cancers and ultimately tailored to specific patients' needs for precision medicine. The disclosed nanostructures can be constructed in minutes and functionalized with therapeutic, stabilizing, and targeting molecules within a few hours.

Advantages of The disclosed nanostructures over current approved lipsosomal-based nanotherapeutics include: 1) unprecedented control of molecular placement allowing for multi-functional modular nanodevices (targeted, simultaneous, and co-localized distribution); 2) tunable and faster drug release rates compared to liposomal encapsulated anthracyclines; 3) ease of fabrication and molecular functionalization; 4) scalability; and 5) biocompatibility and stability.

The disclosed nanostructures can be used as modular cancer drug delivery platform that offers potential therapeutic applications engineered for precision medicine. The disclosed nanostructures may be employed against a host of human diseases (including but not limited to diabetes, heart disease, opportunistic microbial infections, autoimmune diseases) to deliver specific small molecule drugs, therapeutic oligonucleotides, and specific genes in a targeted manner. The disclosed nanostructures also represent a robust experimental drug delivery platform that allows for rapid construction and molecular functionalization.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 7. Schematics of an embodiment modular DNA drug delivery device using either PEGylated oligos (DO-Horse-PEG, left) or PEG molecules attached to lysine residues and attaching to the device by electrostratic interactions (DO-Horse-OLP, right).

FIG. 8. In vivo extended PK of Horse-oligolysine-PEG-(OLP).

DETAILED DESCRIPTION

Figure 1:
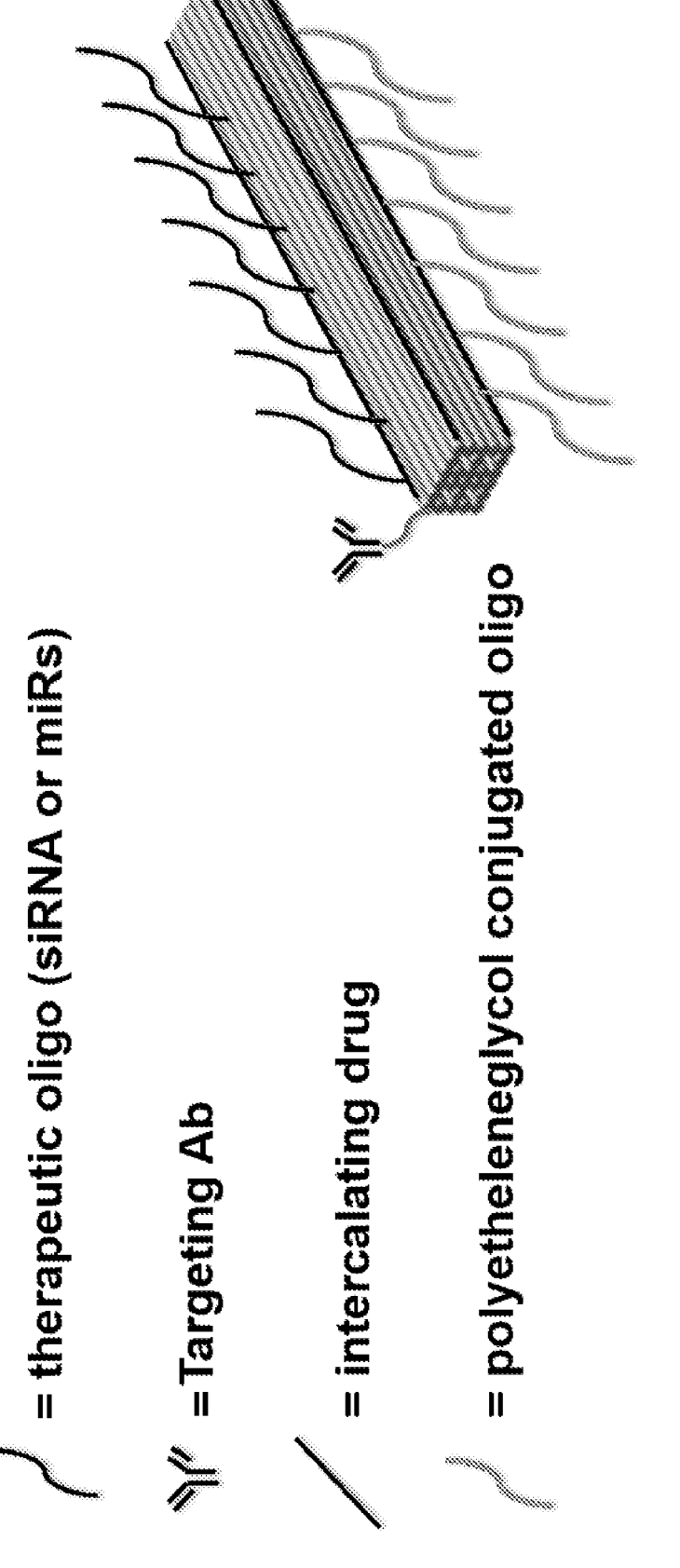
FIG. 1. Design and construction of an embodiment modular DNA drug delivery device disclosed herein based on a DNA origami engineered rod-like nanostructure functionalized with therapeutic oligonucleotides, polyetheleneglycol conjugated oligonucleotides, targeting antibodies, intercalating drugs, and combinations thereof.
Figure 2:
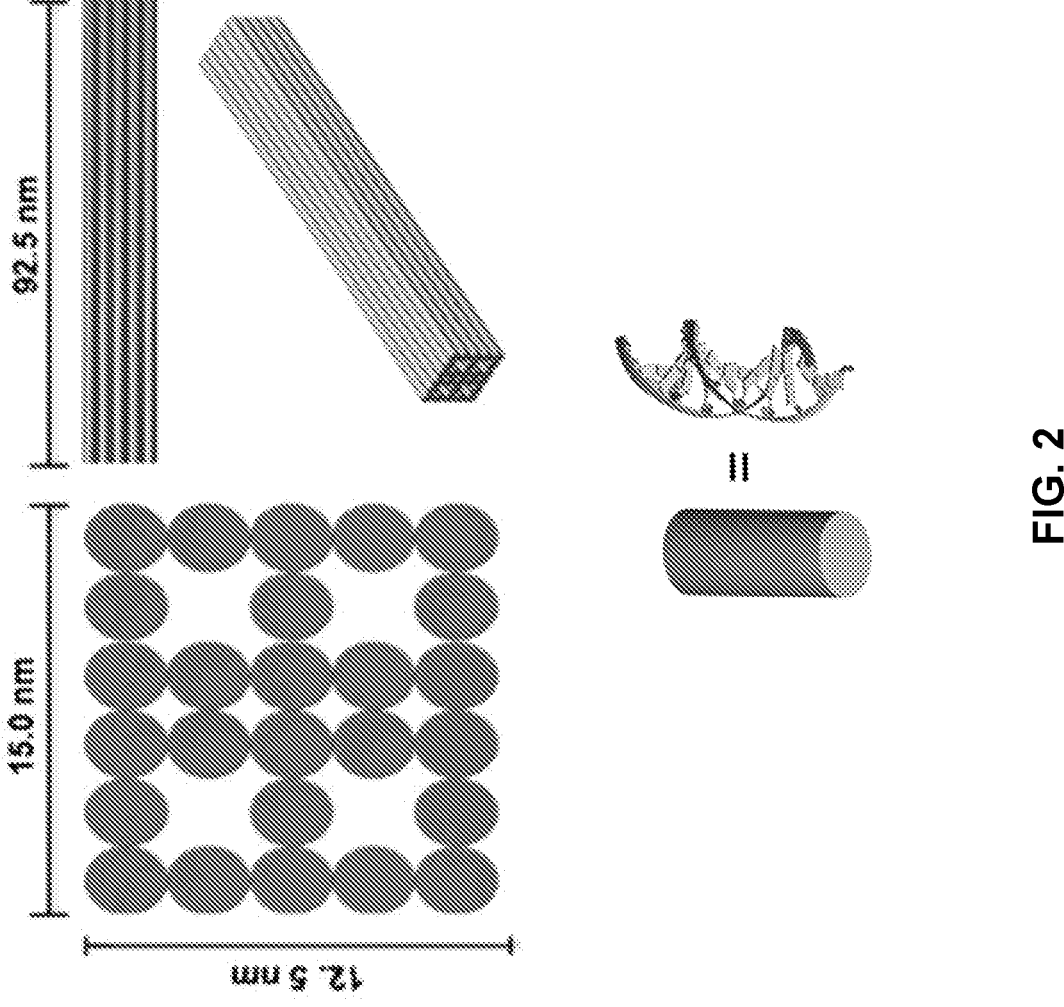
FIG. 2. 2D and 3D design schematics of the DNA origami engineered rod-like nanostructure (approximately 92.5× 13.2×11 nm) containing four open cavities that extend along the length of the structure with a total surface area (approximately 8787.5 $nm^2$).

The disclosed subject matter can be understood more readily by reference to the following detailed description, the Figures, and the examples included herein.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed. As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

It is understood that the disclosed methods and systems are not limited to the particular methodology, protocols, and systems described as these may vary. It is also to be understood that the terminology used herein is for the purpose of describing particular embodiments only, and is not intended to limit the scope of the present invention which will be limited only by the appended claims.

Definitions

Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

As used in the specification and the appended claims, the singular forms "a," "an" and "the" include plural referents unless the context clearly dictates otherwise.

The word "or" as used herein means any one member of a particular list and can also include any combination of members of that list.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, the terms "optional" or "optionally" means that the subsequently described event or circumstance can or can not occur, and that the description includes instances where said event or circumstance occurs and instances where it does not.

As used herein, the term "subject" refers to the target of administration, e.g., an animal. Thus, the subject of the herein disclosed methods can be a vertebrate, such as a mammal, a fish, a bird, a reptile, or an amphibian. Alternatively, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a patient. A patient refers to a subject afflicted with a disease or disorder, such as, for example, cancer and/or aberrant cell growth. The term "patient" includes human and veterinary subjects. In an aspect, the subject has been diagnosed with a need for treatment for cancer and/or aberrant cell growth.

The terms "treating", "treatment", "therapy", and "therapeutic treatment" as used herein refer to curative therapy, prophylactic therapy, or preventative therapy. As used herein, the terms refers to the medical management of a subject or a patient with the intent to cure, ameliorate, stabilize, or prevent a disease, pathological condition, or disorder, such as, for example, cancer or a tumor. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. In various aspects, the term covers any treatment of a subject, including a mammal (e.g., a human), and includes: (i) preventing the disease from occurring in a subject that can be predisposed to the disease but has not yet been diagnosed as having it; (ii) inhibiting the disease, i.e., arresting its development; or (iii) relieving the disease, i.e., causing regression of the disease. In an aspect, the disease, pathological condition, or disorder is cancer, such as, for example, breast cancer, lung cancer, colorectal, liver cancer, or pancreatic cancer. In an aspect, cancer can be any cancer known to the art.

As used herein, the terms "administering" and "administration" refer to any method of providing a composition to a subject. Such methods are well known to those skilled in the art and include, but are not limited to, intracardiac administration, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "contacting" as used herein refers to bringing a disclosed composition or peptide or pharmaceutical preparation and a cell, target receptor, or other biological entity together in such a manner that the compound can affect the activity of the target (e.g., receptor, transcription factor, cell, etc.), either directly; i.e., by interacting with the target itself, or indirectly; i.e., by interacting with another molecule, co-factor, factor, or protein on which the activity of the target is dependent.

As used herein, the terms "effective amount" and "amount effective" refer to an amount that is sufficient to achieve the desired result or to have an effect on an undesired condition. For example, in an aspect, an effective amount of the polymeric nanoparticle is an amount that kills and/or inhibits the growth of cells without causing extraneous damage to surrounding non-cancerous cells. For example, a "therapeutically effective amount" refers to an amount that is sufficient to achieve the desired therapeutic result or to have an effect on undesired symptoms, but is generally insufficient to cause adverse side effects. The specific therapeutically effective dose level for any particular patient will depend upon a variety of factors including the disorder being treated and the severity of the disorder; the specific composition employed; the age, body weight, general health, sex and diet of the patient; the time of administration; the route of administration; the rate of excretion of the specific compound employed; the duration of the treatment; drugs used in combination or coincidental with the specific compound employed and like factors well known in the medical arts.

The term "pharmaceutically acceptable" describes a material that is not biologically or otherwise undesirable, i.e., without causing an unacceptable level of undesirable biological effects or interacting in a deleterious manner. As used herein, the term "pharmaceutically acceptable carrier" refers to sterile aqueous or nonaqueous solutions, dispersions, suspensions or emulsions, as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), carboxymethylcellulose and suitable mixtures thereof, vegetable oils (such as olive oil) and injectable organic esters such as ethyl oleate. Proper fluidity can be maintained, for example, by the use of coating materials such as lecithin, by the maintenance of the required particle size in the case of dispersions and by the use of surfactants. These compositions can also contain adjuvants such as preservatives, wetting agents, emulsifying agents and dispersing agents. Prevention of the action of microorganisms can be ensured by the inclusion of various antibacterial and antifungal agents such as paraben, chlorobutanol, phenol, sorbic acid and the like. It can also be desirable to include isotonic agents such as sugars, sodium chloride and the like. Prolonged absorption of the injectable pharmaceutical form can be brought about by the inclusion of agents, such as aluminum monostearate and gelatin, which delay absorption. Injectable depot forms are made by forming microencapsule matrices of the drug in biodegradable polymers such as polylactide-polyglycolide, poly(orthoesters) and poly(anhydrides). Depending upon the ratio of drug to polymer and the nature of the particular polymer employed, the rate of drug release can be controlled. Depot injectable formulations are also prepared by entrapping the drug in liposomes or microemulsions which are compatible with body tissues. The injectable formulations can be sterilized, for example, by filtration through a bacterial-retaining filter or by incorporating sterilizing agents in the form of sterile solid compositions which can be dissolved or dispersed in sterile water or other sterile injectable media just prior to use. Suitable inert carriers can include sugars such as lactose. Desirably, at least 95% by weight of the particles of the active ingredient have an effective particle size in the range of 0.01 to 10 micrometers.

As used herein, the term "cancer" refers to a proliferative disorder or disease caused or characterized by the proliferation of cells which have lost susceptibility to normal growth control. The term "cancer" includes tumors and any other proliferative disorders. Cancers of the same tissue type originate in the same tissue, and can be divided into different subtypes based on their biological characteristics. Cancer includes, but is not limited to, melanoma, leukemia, astrocytoma, glioblastoma, lymphoma, glioma, Hodgkin's lymphoma, and chronic lymphocyte leukemia. Cancer also includes, but is not limited to, cancer of the brain, bone, pancreas, lung, liver, breast, thyroid, ovary, uterus, testis, pituitary, kidney, stomach, esophagus, anus, and rectum.

The term "DNA origami" refers to nanoscale folding of DNA to create non-arbitrary two- and three-dimensional shapes at the nanoscale. DNA origami works by using a long "scaffold" strand of DNA and holding it together using short, 200-250 base, "staple strands." For example, the origami can be formed using enzymes to cut DNA in certain places on a 5,000-10,000 base strand, inducing the cut pieces into parallel positions and making crossovers, and then using the staple strands to strengthen the structure.

The term "antibody" refers to an immunoglobulin, derivatives thereof which maintain specific binding ability, and proteins having a binding domain which is homologous or largely homologous to an immunoglobulin binding domain. These proteins may be derived from natural sources, or partly or wholly synthetically produced. An antibody may be monoclonal or polyclonal. The antibody may be a member of any immunoglobulin class from any species, including any of the human classes: IgG, IgM, IgA, IgD, and IgE. In exemplary embodiments, antibodies used with the methods and compositions described herein are derivatives of the IgG class. In addition to intact immunoglobulin molecules, also included in the term "antibodies" are fragments or polymers of those immunoglobulin molecules, and human or humanized versions of immunoglobulin molecules that selectively bind the target antigen.

The term "antibody fragment" refers to any derivative of an antibody which is less than full-length. In exemplary embodiments, the antibody fragment retains at least a significant portion of the full-length antibody's specific binding ability. Examples of antibody fragments include, but are not limited to, Fab, Fab', F(ab')2, scFv, Fv, dsFv diabody, Fc, and Fd fragments. The antibody fragment may be produced by any means. For instance, the antibody fragment may be enzymatically or chemically produced by fragmentation of an intact antibody, it may be recombinantly produced from a gene encoding the partial antibody sequence, or it may be wholly or partially synthetically produced. The antibody fragment may optionally be a single chain antibody fragment. Alternatively, the fragment may comprise multiple chains which are linked together, for instance, by disulfide linkages. The fragment may also optionally be a multimolecular complex. A functional antibody fragment will typically comprise at least about 50 amino acids and more typically will comprise at least about 200 amino acids.

The term "antigen binding site" refers to a region of an antibody that specifically binds an epitope on an antigen.

The term "aptamer" refers to oligonucleic acid or peptide molecules that bind to a specific target molecule. These molecules are generally selected from a random sequence pool. The selected aptamers are capable of adapting unique tertiary structures and recognizing target molecules with high affinity and specificity. A "nucleic acid aptamer" is a DNA or RNA oligonucleic acid that binds to a target molecule via its conformation, and thereby inhibits or suppresses functions of such molecule. A nucleic acid aptamer may be constituted by DNA, RNA, or a combination thereof. A "peptide aptamer" is a combinatorial protein molecule with a variable peptide sequence inserted within a constant scaffold protein. Identification of peptide aptamers is typically performed under stringent yeast dihybrid conditions, which enhances the probability for the selected peptide aptamers to be stably expressed and correctly folded in an intracellular context.

DNA Origami Nanostructure

In some embodiments, the disclosed DNA origami nanostructure contains four internal cavities in order to maximize the surface area accessible to solution and allow for a larger cross-section for mechanical stability. Details on how to design and produce these nanostructures are provided in Halley P D, et al. Daunorubicin-Loaded DNA Origami Nanostructures Circumvent Drug-Resistance Mechanisms in a Leukemia Model. Small. 2016 12(3):308-20, which is incorporated by reference herein for these teachings. As shown in Halley P D, et al., staple sequences are included in specific locations within the DNA sequence (see Table 51 or Halley P D, et al.) so that the DNA scaffold folds into a rod-like nanostructure. DNA design software, such as caDNAno, can be used to design 3D DNA origami nanostructures as disclosed herein.

Small Molecule Drugs

The disclosed DNA origami nanostructures can be loaded with any small molecule drug for enhanced drug delivery. In some embodiments, the small molecule drug includes, but is not limited to, a chemotherapeutic drug. In some embodiments, the drug is an anthracyclines, such as doxorubicin, daunorubicin, or idarubicin. In some embodiments, the drug is an alkylating agent. In some embodiments, the drug is an antimetabolite. In some embodiments, the drug is a plant alkaloid. In some embodiments, the drug is a topoisomerase inhibitor.

Therapeutic Nucleic Acids

The disclosed DNA origami nanostructures can be loaded with a therapeutic nucleic acid, such as antisense RNA, microRNAs (miRNAs), short hairpin RNAs (shRNAs), RNA interference (RNAi), and small interfering RNA (siRNA). The disclosed DNA origami nanostructures can be loaded with expression vectors such as plasmids, phagemids, cosmids, or yeast artificial chromosomes (YACs).

Targeting Molecules

For targeted delivery, the disclosed DNA origami nanostructures can be functionalized with a targeting agent specific for a tissue or cancer cell. For example, in some embodiments, the targeting agent is an antibody, aptamer, ligand, or fragment or variant thereof that is able to bind a target antigen or receptor on a tissue or cancer cell. In some embodiments therefore, the targeting agent is an antibody that binds a tumor antigen.

Tumor antigens are proteins that are produced by tumor cells that elicit an immune response, particularly T-cell mediated immune responses. The additional antigen binding domain can be an antibody or a natural ligand of the tumor antigen. The selection of the additional antigen binding domain will depend on the particular type of cancer to be treated. Tumor antigens are well known in the art and include, for example, a glioma-associated antigen, carcinoembryonic antigen (CEA), EGFRvIII, IL-IIRa, IL-13Ra, EGFR, FAP, B7H3, Kit, CA LX, CS-1, MUC1, BCMA, bcr-abl, HER2, β-human chorionic gonadotropin, alphafetoprotein (AFP), ALK, CD19, CD123, cyclin BI, lectin-reactive AFP, Fos-related antigen 1, ADRB3, thyroglobulin, EphA2, RAGE-1, RUI, RU2, SSX2, AKAP-4, LCK, OY-TESI, PAX5, SART3, CLL-1, fucosyl GM1, GloboH, MN-CA IX, EPCAM, EVT6-AML, TGS5, human telomerase reverse transcriptase, plysialic acid, PLAC1, RUI, RU2 (AS), intestinal carboxyl esterase, lewisY, sLe, LY6K, mut hsp70-2, M-CSF, MYCN, RhoC, TRP-2, CYPIBI, BORIS, prostase, prostate-specific antigen (PSA), PAX3, PAP, NY-ESO-1, LAGE-la, LMP2, NCAM, p53, p53 mutant, Ras mutant, gplOO, prostein, OR51E2, PANX3, PSMA, PSCA, Her2/neu, hTERT, HMWMAA, HAVCR1, VEGFR2, PDGFR-beta, survivin and telomerase, legumain, HPV E6,E7, sperm protein 17, SSEA-4, tyrosinase, TARP, WT1, prostate-carcinoma tumor antigen-1 (PCTA-1), ML-IAP, MAGE, MAGE-A1, MAD-CT-1, MAD-CT-2, MelanA/MART 1, XAGE1, ELF2M, ERG (TMPRSS2 ETS fusion gene), NA17, neutrophil elastase, sarcoma translocation breakpoints, NY-BR-1, ephnnB2, CD20, CD22, CD24, CD30, TIM3, CD38, CD44v6, CD97, CD171, CD179a, androgen receptor, FAP, insulin growth factor (IGF)-I, IGFII, IGF-I receptor, GD2, o-acetyl-GD2, GD3, GM3, GPRCSD, GPR20, CXORF61, folate receptor (FRa), folate receptor beta, ROR1, Flt3, TAG72, TN Ag, Tie 2, TEM1, TEM7R, CLDN6, TSHR, UPK2, and mesothelin. In a preferred embodiment, the tumor antigen is selected from the group consisting of folate receptor (FRa), mesothelin, EGFRvIII, IL-13Ra, CD123, CD19, TIM3, BCMA, GD2, CLL-1, CA-IX, MUCI, HER2, and any combination thereof.

Non-limiting examples of tumor antigens include the following: Differentiation antigens such as tyrosinase, TRP-1, TRP-2 and tumor-specific multilineage antigens such as MAGE-1, MAGE-3, BAGE, GAGE-1, GAGE-2, pi 5; over-expressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, pI85erbB2, pI80erbB-3, c-met, nm-23H1, PSA, CA 19-9, CA 72-4, CAM 17.1, NuMa, K-ras, beta-Catenin, CDK4, Mum-1, p 15, p 16, 43-9F, 5T4, 791Tgp72, alphafetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCASI, SDCCAG1 6, TA-90\Mac-2 binding protein\cyclophilm C-associated protein, TAAL6, TAG72, TLP, TPS, GPC3, MUC16, LMP1, EBMA-1, BARF-1, CS1, CD319, HER1, B7H6, L1CAM, IL6, and MET.

Pharmaceutical Formulations

Also provided herein are pharmaceutical formulations that can include an amount of a DNA origami nanostructure described herein and a pharmaceutical carrier appropriate for administration to an individual in need thereof. The individual in need thereof can have or can be suspected of a cancer, a genetic disease or disorder, a viral, bacterial, fungal, and/or parasitic infection, or other disease or disorder in need of treatment or prevention. In some embodiments, the subject in need thereof is in need of a diagnostic procedure, such as an imaging procedure. The pharmaceutical formulations can include an amount of a disclosed DNA origami nanostructures, such as that can be effective to treat or prevent a cancer, a genetic disease or disorder, a viral, bacterial, fungal, and/or parasitic infection, or other disease or disorder or be effective to image the subject or a portion thereof.

Formulations can be administered via any suitable administration route. For example, the formulations (and/or compositions) can be administered to the subject in need thereof orally, intravenously, occularly, intraoccularly, intramuscularly, intravaginally, intraperitoneally, rectally, parenterally, topically, intranasally, or subcutaneously. Other suitable routes are described herein. In some embodimetns, the disclosed DNA origami nanostructures contains an effective amount of a cargo molecule.

Parenteral Formulations

The disclosed DNA origami nanostructures can be formulated for parenteral delivery, such as injection or infusion, in the form of a solution or suspension. The formulation can be administered via any route, such as, the blood stream or directly to the organ or tissue to be treated.

Parenteral formulations can be prepared as aqueous compositions using techniques is known in the art. Typically, such compositions can be prepared as injectable formulations, for example, solutions or suspensions; solid forms suitable for using to prepare solutions or suspensions upon the addition of a reconstitution medium prior to injection; emulsions, such as water-in-oil (w/o) emulsions, oil-in-water (o/w) emulsions, and microemulsions thereof, liposomes, or emulsomes.

The carrier can be a solvent or dispersion medium containing, for example, water, ethanol, one or more polyols (e.g., glycerol, propylene glycol, and liquid polyethylene glycol), oils, such as vegetable oils (e.g., peanut oil, corn oil, sesame oil, etc.), and combinations thereof. The proper fluidity can be maintained, for example, by the use of a coating, such as lecithin, by the maintenance of the required particle size in the case of dispersion and/or by the use of surfactants. In many cases, it will be preferable to include isotonic agents, for example, sugars or sodium chloride.

Solutions and dispersions of the disclosed DNA origami nanostructures can be prepared in water or another solvent or dispersing medium suitably mixed with one or more pharmaceutically acceptable excipients including, but not limited to, surfactants, dispersants, emulsifiers, pH modifying agents, and combination thereof.

Suitable surfactants can be anionic, cationic, amphoteric or nonionic surface active agents. Suitable anionic surfactants include, but are not limited to, those containing carboxylate, sulfonate and sulfate ions. Suitable anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Suitable cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Suitable nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, Poloxamer® 401, stearoyl monoisopropanolamide, and polyoxyethylene hydrogenated tallow amide. Examples of amphoteric surfactants include sodium N-dodecyl-β-alanine, sodium N-lauryl-β-iminodipropionate, myristoamphoacetate, lauryl betaine and lauryl sulfobetaine.

The formulation can contain a preservative to prevent the growth of microorganisms. Suitable preservatives include, but are not limited to, parabens, chlorobutanol, phenol, sorbic acid, and thimerosal. The formulation can also contain an antioxidant to prevent degradation of the disclosed DNA origami nanostructures.

The formulation can be buffered to a pH of 3-8 for parenteral administration upon reconstitution. Suitable buffers include, but are not limited to, phosphate buffers, acetate buffers, and citrate buffers.

Water-soluble polymers can be used in the formulations for parenteral administration. Suitable water-soluble polymers include, but are not limited to, polyvinylpyrrolidone, dextran, carboxymethylcellulose, and polyethylene glycol. Sterile injectable solutions can be prepared by incorporating the disclosed DNA origami nanostructures in the required amount in the appropriate solvent or dispersion medium with one or more of the excipients listed above, as required, followed by filtered sterilization. Dispersions can be prepared by incorporating the various sterilized disclosed DNA origami nanostructures into a sterile vehicle which contains the basic dispersion medium and the required other ingredients from those listed above. Sterile powders for the preparation of sterile injectable solutions can be prepared by vacuum-drying and freeze-drying techniques, which yields a powder of the disclosed DNA origami nanostructures plus any additional desired ingredient from a previously sterile-filtered solution thereof. The powders can be prepared in such a manner that the particles are porous in nature, which can increase dissolution of the particles. Methods for making porous particles are well known in the art.

Pharmaceutical formulations for parenteral administration can be in the form of a sterile aqueous solution or suspension of particles formed from one or more disclosed DNA origami nanostructures. Acceptable solvents include, for example, water, Ringer's solution, phosphate buffered saline (PBS), and isotonic sodium chloride solution. The formulation can also be a sterile solution, suspension, or emulsion in a nontoxic, parenterally acceptable diluent or solvent such as 1,3-butanediol.

In some instances, the formulation can be distributed or packaged in a liquid form. In other embodiments, formulations for parenteral administration can be packed as a solid, obtained, for example by lyophilization of a suitable liquid formulation. The solid can be reconstituted with an appropriate carrier or diluent prior to administration.

Solutions, suspensions, or emulsions for parenteral administration can be buffered with an effective amount of buffer necessary to maintain a pH suitable for ocular administration. Suitable buffers include, but are not limited to, acetate, borate, carbonate, citrate, and phosphate buffers.

Solutions, suspensions, or emulsions for parenteral administration can also contain one or more tonicity agents to adjust the isotonic range of the formulation. Suitable tonicity agents include, but are not limited to, glycerin, mannitol, sorbitol, sodium chloride, and other electrolytes.

Solutions, suspensions, or emulsions for parenteral administration can also contain one or more preservatives to prevent bacterial contamination of the ophthalmic preparations. Suitable preservatives include, but are not limited to, polyhexamethylenebiguanidine (PHMB), benzalkonium chloride (BAK), stabilized oxychloro complexes (otherwise known as Purite®), phenylmercuric acetate, chlorobutanol, sorbic acid, chlorhexidine, benzyl alcohol, parabens, thimerosal, and mixtures thereof.

Solutions, suspensions, or emulsions, use of nanotechnology including nanoformulations for parenteral administration can also contain one or more excipients, such as dispersing agents, wetting agents, and suspending agents.

Topical Formulations

The disclosed DNA origami nanostructures can be formulated for topical administration. Suitable dosage forms for topical administration include creams, ointments, salves, sprays, gels, lotions, emulsions, liquids, and transdermal patches. The formulation can be formulated for transmucosal, transepithelial, transendothelial, or transdermal administration. The topical formulations can contain one or more chemical penetration enhancers, membrane permeability agents, membrane transport agents, emollients, surfactants, stabilizers, and combination thereof.

In some embodiments, the disclosed DNA origami nanostructures can be administered as a liquid formulation, such as a solution or suspension, a semi-solid formulation, such as a lotion or ointment, or a solid formulation. In some embodiments, the disclosed DNA origami nanostructures can be formulated as liquids, including solutions and suspensions, such as eye drops or as a semi-solid formulation, such as ointment or lotion for topical application to the skin, to the mucosa, such as the eye, to the vagina, or to the rectum.

The formulation can contain one or more excipients, such as emollients, surfactants, emulsifiers, penetration enhancers, and the like.

Suitable emollients include, without limitation, almond oil, castor oil, Ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In some embodiments, the emollients can be ethylhexylstearate and ethylhexyl palmitate.

Suitable surfactants include, but are not limited to, emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In some embodiments, the surfactant can be stearyl alcohol.

Suitable emulsifiers include, but are not limited to, acacia, metallic soaps, certain animal and vegetable oils, and various polar compounds, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In some embodiments, the emulsifier can be glycerol stearate.

Suitable classes of penetration enhancers include, but are not limited to, fatty alcohols, fatty acid esters, fatty acids, fatty alcohol ethers, amino acids, phospholipids, lecithins, cholate salts, enzymes, amines and amides, complexing agents (liposomes, cyclodextrins, modified celluloses, and diimides), macrocyclics, such as macrocylic lactones, ketones, and anhydrides and cyclic ureas, surfactants, N-methyl pyrrolidones and derivatives thereof, DMSO and related compounds, ionic compounds, azone and related compounds, and solvents, such as alcohols, ketones, amides, polyols (e.g., glycols).

Suitable emulsions include, but are not limited to, oil-in-water and water-in-oil emulsions. Either or both phases of the emulsions can include a surfactant, an emulsifying agent, and/or a liquid non-volatile non-aqueous material. In some embodiments, the surfactant can be a non-ionic surfactant. In other embodiments, the emulsifying agent is an emulsifying wax. In further embodiments, the liquid non-volatile non-aqueous material is a glycol. In some embodiments, the glycol is propylene glycol. The oil phase can contain other suitable oily pharmaceutically acceptable excipients. Suitable oily pharmaceutically acceptable excipients include, but are not limited to, hydroxylated castor oil or sesame oil can be used in the oil phase as surfactants or emulsifiers.

Lotions containing a disclosed DNA origami nanostructures are also provided. In some embodiments, the lotion can be in the form of an emulsion having a viscosity of between 100 and 1000 centistokes. The fluidity of lotions can permit rapid and uniform application over a wide surface area. Lotions can be formulated to dry on the skin leaving a thin coat of their medicinal components on the skin's surface.

Creams containing a disclosed DNA origami nanostructures as described herein are also provided. The cream can contain emulsifying agents and/or other stabilizing agents. In some embodiments, the cream is in the form of a cream having a viscosity of greater than 1000 centistokes, typically in the range of 20,000-50,000 centistokes. Creams, as compared to ointments, can be easier to spread and easier to remove.

One difference between a cream and a lotion is the viscosity, which is dependent on the amount/use of various oils and the percentage of water used to prepare the formulations. Creams can be thicker than lotions, can have various uses, and can have more varied oils/butters, depending upon the desired effect upon the skin. In some embodiments of a cream formulation, the water-base percentage can be about 60% to about 75% and the oil-base can be about 20% to about 30% of the total, with the other percentages being the emulsifier agent, preservatives and additives for a total of 100%.

Ointments containing a disclosed DNA origami nanostructures as described herein and a suitable ointment base are also provided. Suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

Also described herein are gels containing a disclosed DNA origami nanostructures as described herein, a gelling agent, and a liquid vehicle. Suitable gelling agents include, but are not limited to, modified celluloses, such as hydroxypropyl cellulose and hydroxyethyl cellulose; carbopol homopolymers and copolymers; thermoreversible gels and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents can be selected for their ability to dissolve the drug. Other additives, which can improve the skin feel and/or emolliency of the formulation, can also be incorporated. Such additives include, but are not limited, isopropyl myristate, ethyl acetate, $C_{12}$-$C_{15}$ alkyl benzoates, mineral oil, squalane, cyclomethicone, capric/caprylic triglycerides, and combinations thereof.

Also described herein are foams that can include a disclosed DNA origami nanostructures as described herein. Foams can be an emulsion in combination with a gaseous propellant. The gaseous propellant can include hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or can become approved for medical use are suitable. The propellants can be devoid of hydrocarbon propellant gases, which can produce flammable or explosive vapors during spraying. Furthermore, the foams can contain no volatile alcohols, which can produce flammable or explosive vapors during use.

Buffers can be used to control pH of a composition. The buffers can buffer the composition from a pH of about 4 to a pH of about 7.5, from a pH of about 4 to a pH of about 7, or from a pH of about 5 to a pH of about 7. In some embodiments, the buffer can be triethanolamine.

Preservatives can be included to prevent the growth of fungi and microorganisms. Suitable preservatives include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

In certain embodiments, the formulations can be provided via continuous delivery of one or more formulations to a patient in need thereof. For topical applications, repeated application can be done or a patch can be used to provide continuous administration of the noscapine analogs over an extended period of time.

Enteral Formulations

The disclosed DNA origami nanostructures can be prepared in enteral formulations, such as for oral administration. Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Formulations containing a disclosed DNA origami nanostructures can be prepared using pharmaceutically acceptable carriers. As generally used herein "carrier" includes, but is not limited to, diluents, preservatives, binders, lubricants, disintegrators, swelling agents, fillers, stabilizers, and combinations thereof. Polymers used in the dosage form include, but are not limited to, suitable hydrophobic or hydrophilic polymers and suitable pH dependent or independent polymers. Suitable hydrophobic and hydrophilic polymers include, but are not limited to, hydroxypropyl methylcellulose, hydroxypropyl cellulose, hydroxyethyl cellulose, carboxy methylcellulose, polyethylene glycol, ethylcellulose, microcrystalline cellulose, polyvinyl pyrrolidone, polyvinyl alcohol, polyvinyl acetate, and ion exchange resins. "Carrier" also includes all components of the coating composition which can include plasticizers, pigments, colorants, stabilizing agents, and glidants.

Formulations containing a disclosed DNA origami nanostructures can be prepared using one or more pharmaceutically acceptable excipients, including diluents, preservatives, binders, lubricants, disintegrators, swelling agents, fillers, stabilizers, and combinations thereof.

Delayed release dosage formulations containing a disclosed DNA origami nanostructures can be prepared as described in standard references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, MD, 2000, and "Pharmaceutical dosage forms and drug delivery systems", 6th Edition, Ansel et al., (Media, PA: Williams and Wilkins, 1995). These references provide information on excipients, materials, equipment and process for preparing tablets and capsules and delayed release dosage forms of tablets, capsules, and granules. These references provide information on carriers, materials, equipment and process for preparing tablets and capsules and delayed release dosage forms of tablets, capsules, and granules.

The formulations containing a disclosed DNA origami nanostructures can be coated with a suitable coating material, for example, to delay release once the particles have passed through the acidic environment of the stomach. Suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name EUDRAGIT® (Roth Pharma, Westerstadt, Germany), zein, shellac, and polysaccharides.

Coatings can be formed with a different ratio of water soluble polymer, water insoluble polymers and/or pH dependent polymers, with or without water insoluble/water soluble non polymeric excipient, to produce the desired release profile. The coating can be performed on a dosage form (matrix or simple) which includes, but is not limited to, tablets (compressed with or without coated beads), capsules (with or without coated beads), beads, particle compositions, "ingredient as is" formulated as, but not limited to, suspension form or as a sprinkle dosage form.

Additionally, the coating material can contain conventional carriers such as plasticizers, pigments, colorants, glidants, stabilization agents, pore formers and surfactants. Optional pharmaceutically acceptable excipients include, but are not limited to, diluents, binders, lubricants, disintegrants, colorants, stabilizers, and surfactants.

Diluents, also referred to as "fillers," can be used to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powdered sugar. The usual diluents include inert powdered substances such as starches, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful.

Binders can impart cohesive qualities to a solid dosage formulation, and thus can ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydroxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone. Typical tablet binders include substances such as starch, gelatin and sugars such as lactose, fructose, and glucose. Natural and synthetic gums, including acacia, alginates, methylcellulose, and polyvinylpyrrolidone can also be used. Polyethylene glycol, hydrophilic polymers, ethylcellulose and waxes can also serve as binders.

Lubricants can be included to facilitate tablet manufacture. Suitable lubricants include, but are not limited to, magnesium stearate, calcium stearate, stearic acid, glycerol behenate, polyethylene glycol, talc, and mineral oil. A lubricant can be included in a tablet formulation to prevent the tablet and punches from sticking in the die. The lubricant can be chosen from such slippery solids as talc, magnesium and calcium stearate, stearic acid and hydrogenated vegetable oils.

Disintegrants can be used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone® XL from GAF Chemical Corp).

Stabilizers can be used to inhibit or retard drug decomposition reactions which include, by way of example, oxidative reactions. Suitable stabilizers include, but are not limited to, antioxidants, butylated hydroxytoluene (BHT); ascorbic acid, its salts and esters; Vitamin E, tocopherol and its salts; sulfites such as sodium metabisulphite; cysteine and its derivatives; citric acid; propyl gallate, and butylated hydroxyanisole (BHA).

Additional Active Agents

In some embodiments, an amount of one or more additional active agents are included in the pharmaceutical formulation containing a disclosed DNA origami nanostructures. Suitable additional active agents include, but are not limited to, DNA, RNA, amino acids, peptides, polypeptides, antibodies, aptamers, ribozymes, guide sequences for ribozymes that inhibit translation or transcription of essential tumor proteins and genes, hormones, immunomodulators, antipyretics, anxiolytics, antipsychotics, analgesics, antispasmodics, anti-inflammatories, anti-histamines, anti-infectives, and chemotherapeutics (anti-cancer drugs). Other suitable additional active agents include, sensitizers (such as radiosensitizers). The disclosed DNA origami nanostructures can be used as a monotherapy or in combination with other active agents for treatment or prevention of a disease or disorder.

Suitable hormones include, but are not limited to, amino-acid derived hormones (e.g. melatonin and thyroxine), small peptide hormones and protein hormones (e.g. thyrotropin-releasing hormone, vasopressin, insulin, growth hormone, luteinizing hormone, follicle-stimulating hormone, and thyroid-stimulating hormone), eiconsanoids (e.g. arachidonic acid, lipoxins, and prostaglandins), and steroid hormones (e.g. estradiol, testosterone, tetrahydro testosteron cortisol).

Suitable immunomodulators include, but are not limited to, prednisone, azathioprine, 6-MP, cyclosporine, tacrolimus, methotrexate, interleukins (e.g. IL-2, IL-7, and IL-12), cytokines (e.g. interferons (e.g. IFN-α, IFN-β, IFN-ε, IFN-κ, IFN-ω, and IFN-γ), granulocyte colony-stimulating factor, and imiquimod), chemokines (e.g. CCL3, CCL26 and CXCL7), cytosine phosphate-guanosine, oligodeoxynucleotides, glucans, antibodies, and aptamers).

Suitable antipyretics include, but are not limited to, non-steroidal anti-inflammants (e.g. ibuprofen, naproxen, ketoprofen, and nimesulide), aspirin and related salicylates (e.g. choline salicylate, magnesium salicylae, and sodium salicaylate), paracetamol/acetaminophen, metamizole, nabumetone, phenazone, and quinine.

Suitable anxiolytics include, but are not limited to, benzodiazepines (e.g. alprazolam, bromazepam, chlordiazepoxide, clonazepam, clorazepate, diazepam, flurazepam, lorazepam, oxazepam, temazepam, triazolam, and tofisopam), serotenergic antidepressants (e.g. selective serotonin reuptake inhibitors, tricyclic antidepresents, and monoamine oxidase inhibitors), mebicar, afobazole, selank, bromantane, emoxypine, azapirones, barbituates, hyxdroxyzine, pregabalin, validol, and beta blockers.

Suitable antipsychotics include, but are not limited to, benperidol, bromoperidol, droperidol, haloperidol, moperone, pipaperone, timiperone, fluspirilene, penfluridol, pimozide, acepromazine, chlorpromazine, cyamemazine, dizyrazine, fluphenazine, levomepromazine, mesoridazine, perazine, pericyazine, perphenazine, pipotiazine, prochlorperazine, promazine, promethazine, prothipendyl, thioproperazine, thioridazine, trifluoperazine, triflupromazine, chlorprothixene, clopenthixol, flupentixol, tiotixene, zuclopenthixol, clotiapine, loxapine, prothipendyl, carpipramine, clocapramine, molindone, mosapramine, sulpiride, veralipride, amisulpride, amoxapine, aripiprazole, asenapine, clozapine, blonanserin, iloperidone, lurasidone, melperone, nemonapride, olanzaprine, paliperidone, perospirone, quetiapine, remoxipride, risperidone, sertindole, trimipramine, ziprasidone, zotepine, alstonie, befeprunox, bitopertin, brexpiprazole, cannabidiol, cariprazine, pimavanserin, pomaglumetad methionil, vabicaserin, xanomeline, and zicronapine.

Suitable analgesics include, but are not limited to, paracetamol/acetaminophen, non-steroidal anti-inflammants (e.g. ibuprofen, naproxen, ketoprofen, and nimesulide), COX-2 inhibitors (e.g. rofecoxib, celecoxib, and etoricoxib), opioids (e.g. morphine, codeine, oxycodone, hydrocodone, dihydromorphine, pethidine, buprenorphine), tramadol, norepinephrine, flupiretine, nefopam, orphenadrine, pregabalin, gabapentin, cyclobenzaprine, scopolamine, methadone, ketobemidone, piritramide, and aspirin and related salicylates (e.g. choline salicylate, magnesium salicylae, and sodium salicaylate).

Suitable antispasmodics include, but are not limited to, mebeverine, papverine, cyclobenzaprine, carisoprodol, orphenadrine, tizanidine, metaxalone, methodcarbamol, chlorzoxazone, baclofen, dantrolene, baclofen, tizanidine, and dantrolene.

Suitable anti-inflammatories include, but are not limited to, prednisone, non-steroidal anti-inflammants (e.g. ibuprofen, naproxen, ketoprofen, and nimesulide), COX-2 inhibitors (e.g. rofecoxib, celecoxib, and etoricoxib), and immune selective anti-inflammatory derivatives (e.g. submandibular gland peptide-T and its derivatives).

Suitable anti-histamines include, but are not limited to, $H_1$-receptor antagonists (e.g. acrivastine, azelastine, bilastine, brompheniramine, buclizine, bromodiphenhydramine, carbinoxamine, cetirizine, chlorpromazine, cyclizine, chlorpheniramine, clemastine, cyproheptadine, desloratadine, dexbromapheniramine, dexchlorpheniramine, dimenhydrinate, dimetindene, diphenhydramine, doxylamine, ebasine, embramine, fexofenadine, hydroxyzine, levocetirzine, loratadine, meclozine, mirtazapine, olopatadine, orphenadrine, phenindamine, pheniramine, phenyltoloxamine, promethazine, pyrilamine, quetiapine, rupatadine, tripelennamine, and triprolidine), $H_2$-receptor antagonists (e.g. cimetidine, famotidine, lafutidine, nizatidine, rafitidine, and roxatidine), tritoqualine, catechin, cromoglicate, nedocromil, and β2-adrenergic agonists.

Suitable anti-infectives include, but are not limited to, amebicides (e.g. nitazoxanide, paromomycin, metronidazole, tnidazole, chloroquine, and iodoquinol), aminoglycosides (e.g. paromomycin, tobramycin, gentamicin, amikacin, kanamycin, and neomycin), anthelmintics (e.g. pyrantel, mebendazole, ivermectin, praziquantel, abendazole, miltefosine, thiabendazole, oxamniquine), antifungals (e.g. azole antifungals (e.g. itraconazole, fluconazole, posaconazole, ketoconazole, clotrimazole, miconazole, and voriconazole), echinocandins (e.g. caspofungin, anidulafungin, and micafungin), griseofulvin, terbinafine, flucytosine, and polyenes (e.g. nystatin, and amphotericin b), antimalarial agents (e.g. pyrimethamine/sulfadoxine, artemether/lumefantrine, atovaquone/proquanil, quinine, hydroxychloroquine, mefloquine, chloroquine, doxycycline, pyrimethamine, and halofantrine), antituberculosis agents (e.g. aminosalicylates (e.g. aminosalicylic acid), isoniazid/rifampin, isoniazid/pyrazinamide/rifampin, bedaquiline, isoniazid, ethanmbutol, rifampin, rifabutin, rifapentine, capreomycin, and cycloserine), antivirals (e.g. amantadine, rimantadine, abacavir/lamivudine, emtricitabine/tenofovir, cobicistat/elvitegravir/emtricitabine/tenofovir, efavirenz/emtricitabine/tenofovir, avacavir/lamivudine/zidovudine, lamivudine/zidovudine, emtricitabine/tenofovir, emtricitabine/opinavir/ritonavir/tenofovir, interferon alfa-2v/ribavirin, peginterferon alfa-2b, maraviroc, raltegravir, dolutegravir, enfuvirtide, foscarnet, fomivirsen, oseltamivir, zanamivir, nevirapine, efavirenz, etravirine, rilpiviirine, delaviridine, nevirapine, entecavir, lamivudine, adefovir, sofosbuvir, didanosine, tenofovir, avacivr, zidovudine, stavudine, emtricitabine, xalcitabine, telbivudine, simeprevir, boceprevir, telaprevir, lopinavir/ritonavir, fosamprenvir, dranuavir, ritonavir, tipranavir, atazanavir, nelfinavir, amprenavir, indinavir, sawuinavir, ribavirin, valcyclovir, acyclovir, famciclovir, ganciclovir, and valganciclovir), carbapenems (e.g. doripenem, meropenem, ertapenem, and cilastatin/imipenem), cephalosporins (e.g. cefadroxil, cephradine, cefazolin, cephalexin, cefepime, ceflaroline, loracarbef, cefotetan, cefuroxime, cefprozil, loracarbef, cefoxitin, cefaclor, ceftibuten, ceftriaxone, cefotaxime, cefpodoxime, cefdinir, cefixime, cefditoren, cefizoxime, and ceftazidime), glycopeptide antibiotics (e.g. vancomycin, dalbavancin, oritavancin, and telvancin), glycylcyclines (e.g. tigecycline), leprostatics (e.g. clofazimine and thalidomide), lincomycin and derivatives thereof (e.g. clindamycin and lincomycin), macrolides and derivatives thereof (e.g. telithromycin, fidaxomicin, erthromycin, azithromycin, clarithromycin, dirithromycin, and troleandomycin), linezolid, sulfamethoxazole/trimethoprim, rifaximin, chloramphenicol, fosfomycin, metronidazole, aztreonam, bacitracin, beta lactam antibiotics (benzathine penicillin (benzatihine and benzylpenicillin), phenoxymethylpenicillin, cloxacillin, flucoxacillin, methicillin, temocillin, mecillinam, azlocillin, mezlocillin, piperacillin, amoxicillin, ampicillin, bacampicillin, carbenicillin, piperacillin, ticarcillin, amoxicillin/clavulanate, ampicillin/sulbactam, piperacillin/tazobactam, clavulanate/ticarcillin, penicillin, procaine penicillin, oxacillin, dicloxacillin, nafcillin, cefazolin, cephalexin, cephalosporin C, cephalothin, cefaclor, cefamandole, cefuroxime, cefotetan, cefoxitin, cefiximine, cefotaxime, cefpodoxime, ceftazidime, ceftriaxone, cefepime, cefpirome, ceftaroline, biapenem, doripenem, ertapenem, faropenem, imipenem, meropenem, panipenem, razupenem, tebipenem, thienamycin, azrewonam, tigemonam, nocardicin A, taboxinine, and beta-lactam), quinolones (e.g. lomefloxacin, norfloxacin, ofloxacin, qatifloxacin, moxifloxacin, ciprofloxacin, levofloxacin, gemifloxacin, moxifloxacin, cinoxacin, nalidixic acid, enoxacin, grepafloxacin, gatifloxacin, trovafloxacin, and sparfloxacin), sulfonamides (e.g. sulfamethoxazole/trimethoprim, sulfasalazine, and sulfasoxazole), tetracyclines (e.g. doxycycline, demeclocycline, minocycline, doxycycline/salicyclic acid, doxycycline/omega-3 polyunsaturated fatty acids, and tetracycline), and urinary anti-infectives (e.g. nitrofurantoin, methenamine, fosfomycin, cinoxacin, nalidixic acid, trimethoprim, and methylene blue).

Suitable chemotherapeutics include, but are not limited to, paclitaxel, brentuximab vedotin, doxorubicin, 5-FU (fluorouracil), everolimus, pemetrexed, melphalan, pamidronate, anastrozole, exemestane, nelarabine, ofatumumab, bevacizumab, belinostat, tositumomab, carmustine, bleomycin, bosutinib, busulfan, alemtuzumab, irinotecan, vandetanib, bicalutamide, lomustine, daunorubicin, clofarabine, cabozantinib, dactinomycin, ramucirumab, cytarabine, cytoxan, cyclophosphamide, decitabine, dexamethasone, docetaxel, hydroxyurea, decarbazine, leuprolide, epirubicin, oxaliplatin, asparaginase, estramustine, cetuximab, vismodegib, aspargainase *erwinia* chyrsanthemi, amifostine, etoposide, flutamide, toremifene, fulvestrant, letrozole, degarelix, pralatrexate, methotrexate, floxuridine, obinutuzumab, gemcitabine, afatinib, imatinib mesylatem, carmustine, eribulin, trastuzumab, altretamine, topotecan, ponatinib, idarubicin, ifosfamide, ibrutinib, axitinib, interferon alfa-2a, gefitinib, romidepsin, ixabepilone, ruxolitinib, cabazitaxel, ado-trastuzumab emtansine, carfilzomib, chlorambucil, sargramostim, cladribine, mitotane, vincristine, procarbazine, megestrol, trametinib, mesna, strontium-89 chloride, mechlorethamine, mitomycin, busulfan, gemtuzumab ozogamicin, vinorelbine, filgrastim, pegfilgrastim, sorafenib, nilutamide, pentostatin, tamoxifen, mitoxantrone, pegaspargase, denileukin diftitox, alitretinoin, carboplatin, pertuzumab, cisplatin, pomalidomide, prednisone, aldesleukin, mercaptopurine, zoledronic acid, lenalidomide, rituximab, octretide, dasatinib, regorafenib, histrelin, sunitinib, siltuximab, omacetaxine, thioguanine (tioguanine), dabrafenib, erlotinib, bexarotene, temozolomide, thiotepa, thalidomide, BCG, temsirolimus, bendamustine hydrochloride, triptorelin, aresnic trioxide, lapatinib, valrubicin, panitumumab, vinblastine, bortezomib, tretinoin, azacitidine, pazopanib, teniposide, leucovorin, crizotinib, capecitabine, enzalutamide, ipilimumab, goserelin, vorinostat, idelalisib, ceritinib, abiraterone, epothilone, tafluposide, azathioprine, doxifluridine, vindesine, all-trans retinoic acid, and other anti-cancer agents listed elsewhere herein.

Methods of Using DNA Origami Nanostructures

The disclosed DNA origami nanostructures can be used to deliver one or more cargo compounds to a subject in need thereof or a cell. In some embodiments, the disclosed DNA origami nanostructures can be used to deliver an RNA or DNA molecule for replacement gene/transcript therapy, deliver RNAi or similar RNA (e.g. microRNA) to a subject to specifically inhibit RNA transcripts to reduce gene expression of a specific gene or genes, deliver an imaging agent, delivering a small molecule drug, and/or deliver any other cargo compound that can be loaded in the disclosed DNA origami nanostructures. Thus, the disclosed DNA origami nanostructures can be used to deliver a treatment, prevention, and/or a diagnostic compound to a subject in need thereof.

The disclosed DNA origami nanostructures can be used in some cases to treat a subject with a cancer. The cancer of the disclosed methods can be any cell in a subject undergoing unregulated growth, invasion, or metastasis. In some aspects, the cancer can be any neoplasm or tumor for which radiotherapy is currently used. Alternatively, the cancer can be a neoplasm or tumor that is not sufficiently sensitive to radiotherapy using standard methods. Thus, the cancer can be a sarcoma, lymphoma, leukemia, carcinoma, blastoma, or germ cell tumor. A representative but non-limiting list of cancers that the disclosed compositions can be used to treat include lymphoma, B cell lymphoma, T cell lymphoma, mycosis fungoides, Hodgkin's Disease, myeloid leukemia, bladder cancer, brain cancer, nervous system cancer, head and neck cancer, squamous cell carcinoma of head and neck, kidney cancer, lung cancers such as small cell lung cancer and non-small cell lung cancer, neuroblastoma/glioblastoma, ovarian cancer, pancreatic cancer, prostate cancer, skin cancer, liver cancer, melanoma, squamous cell carcinomas of the mouth, throat, larynx, and lung, colon cancer, cervical cancer, cervical carcinoma, breast cancer, epithelial cancer, renal cancer, genitourinary cancer, pulmonary cancer, esophageal carcinoma, head and neck carcinoma, large bowel cancer, hematopoietic cancers; testicular cancer; colon and rectal cancers, prostatic cancer, and pancreatic cancer.

In some embodiments, where the disclosed DNA origami nanostructures include a photocleavable linker that is linking the targeting moiety and/or cargo compound the DNA origami nanostructures can be administered to the subject or population of cells. After administration, light can be applied to the region and/or population of cells in the subject in need thereof where treatment or prevention is needed to cause the release of the disclosed DNA origami nanostructures and/or cargo molecule.

The disclosed DNA origami nanostructures as provided herein can be administered to a subject in need thereof, cell, or population thereof. The subject in need thereof can have a cancer, genetic disease or disorder, a viral, bacterial, parasitic, and/or fungal infection, or any other disease or disorder that would benefit from an effective agent (such as a cargo compound described herein) being delivered. The amount delivered can be an effective amount of a DNA origami nanostructures provided herein. The subject in need thereof can be symptomatic or asymptomatic. In some embodiments, the DNA origami nanostructures provided herein can be co-administered with another active agent. It will be appreciated that co-administered can refer to an additional compound that is included in the formulation or provided in a dosage form separate from the DNA origami nanostructures or formulation thereof. The effective amount of the DNA origami nanostructures or formulation thereof, such as those described herein, can range from about 0.1 mg/kg to about 500 mg/kg. In some embodiments, the effective amount ranges from about 0.1 mg/kg to 10 mg/kg. In additional embodiments, the effective amount ranges from about 100 mg/kg. If further embodiments, the effective amount ranges from about 0.1 mg to about 1000 mg. In some embodiments, the effective amount can be about 500 mg to about 1000 mg.

Administration of the DNA origami nanostructures and formulations thereof can be systemic or localized. The compounds and formulations described herein can be administered to the subject in need thereof one or more times per day. In an embodiment, the compound(s) and/or formulation(s) thereof can be administered once daily. In some embodiments, the compound(s) and/or formulation(s) thereof can be administered given once daily. In another embodiment, the compound(s) and/or formulation(s) thereof can be administered is administered twice daily. In some embodiments, when administered, an effective amount of the compounds and/or formulations are administered to the subject in need thereof. The compound(s) and/or formulation(s) thereof can be administered one or more times per week. In some embodiments the compound(s) and/or formulation(s) thereof can be administered 1 day per week. In other embodiments, the compound(s) and/or formulation(s) thereof can be administered 2 to 7 days per week.

In some embodiments, the DNA origami nanostructures(s) and/or formulation(s) thereof, can be administered in a dosage form. The amount or effective amount of the compound(s) and/or formulation(s) thereof can be divided into multiple dosage forms. For example, the effective amount can be split into two dosage forms and the one dosage forms can be administered, for example, in the morning, and the second dosage form can be administered in the evening. Although the effective amount is given over two doses, in one day, the subject receives the effective amount. In some embodiments the effective amount is about 0.1 to about 1000 mg per day. The effective amount in a dosage form can range from about 0.1 mg/kg to about 1000 mg/kg. The dosage form can be formulated for oral, vaginal, intravenous, transdermal, subcutaneous, intraperitoneal, or intramuscular administration. Preparation of dosage forms for various administration routes are described elsewhere herein.

A number of embodiments of the invention have been described. Nevertheless, it will be understood that various modifications may be made without departing from the spirit and scope of the invention. Accordingly, other embodiments are within the scope of the following claims.

EXAMPLES

Example 1

Two DNA origami nanostructures were evaluated that vary in shape, a flat-2D triangle and 3D-rod-shaped nanostructure either alone or functionalized with polyethyleneglycol (PEG)-conjugated oligonucleotides. A repeat dosing regimen of unloaded triangle and rod-shaped structures at clinically relevant levels revealed that DNA origami nanostructures were generally non-toxic in vivo as shown by weight and a complete biochemical panel assessing liver function apart from mild hepatic necrosis in mice treated with PEG-coated triangle nanostructures. A modest proinflammatory molecular and cellular immune response was evident among mice in all treatment groups, especially among mice treated with triangle/triangle-PEG that dampened by the conclusion of the dosing regimen. Distribution findings thus far show PEG-functionalized and non-functionalized DNA nanostructures distribute throughout the periphery immediately after i.v. injection and within ~30 minutes after i.p. injection, while myeloid cell populations internalized DNA nanostructures ex vivo. We hypothesize that our PEG-functionalized DNA nanostructures will have increased stability in vivo relative to unmodified DNA nanostructures and may be evaluated via a fluorescence-based live animal in vivo imaging system (IVIS). Taken together, in vivo findings suggest that DNA origami nanostructures are mostly non-toxic, distribute effectively into the periphery, generate a modest immune response, and, therefore represent a promising novel platform for future cancer drug delivery studies in vivo.

Example 2

Figure 3:
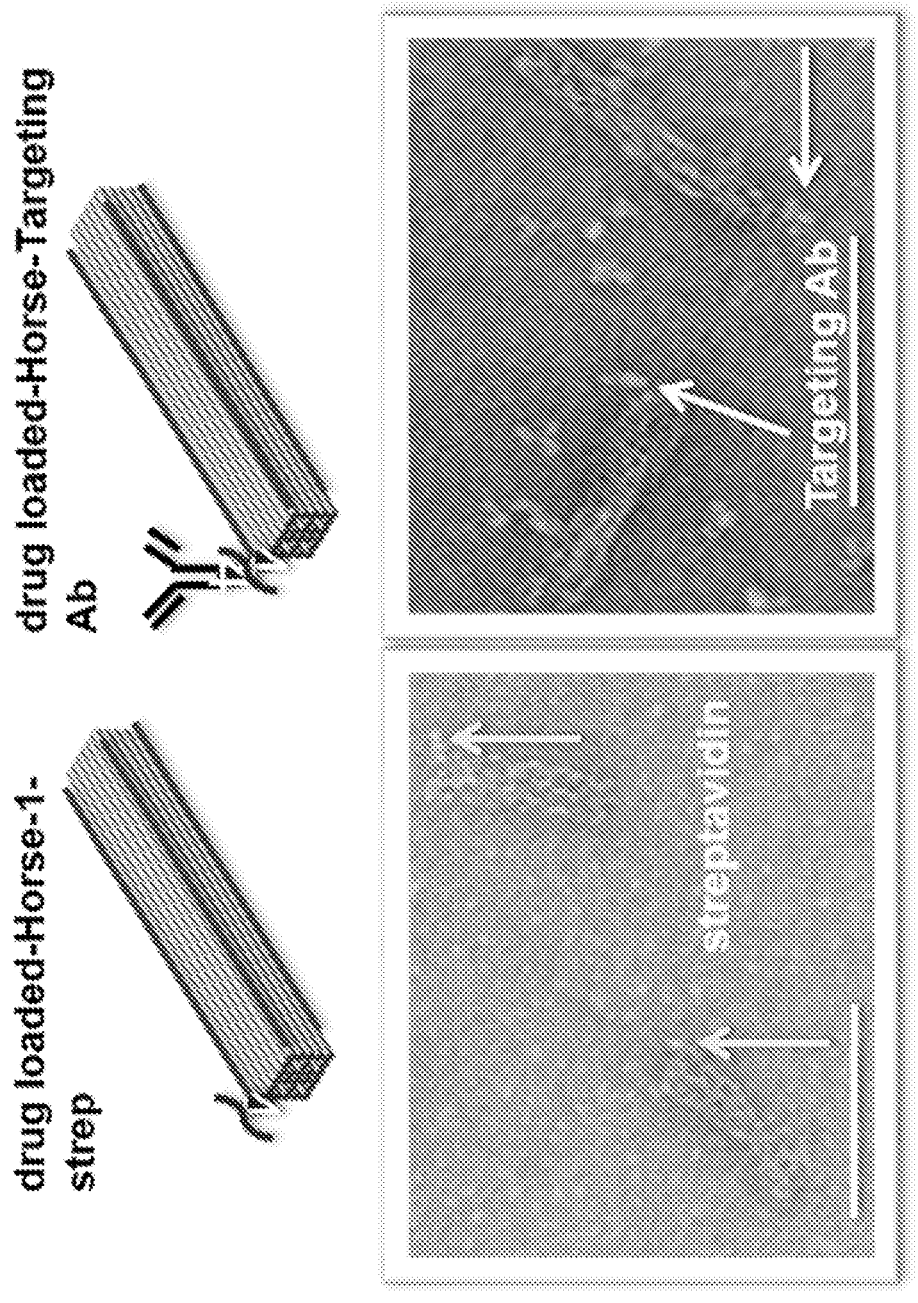
FIG. 3. Schematics and images of drug-loaded delivery devices functionalized with streptavidin (left) and a targeting antibody (right). Scale bars, 100 nm.

FIG. 3. Schematics and images of drug-loaded delivery devices functionalized with streptavidin (left) and a targeting antibody (right). Scale bars, 100 nm.

Figure 4:
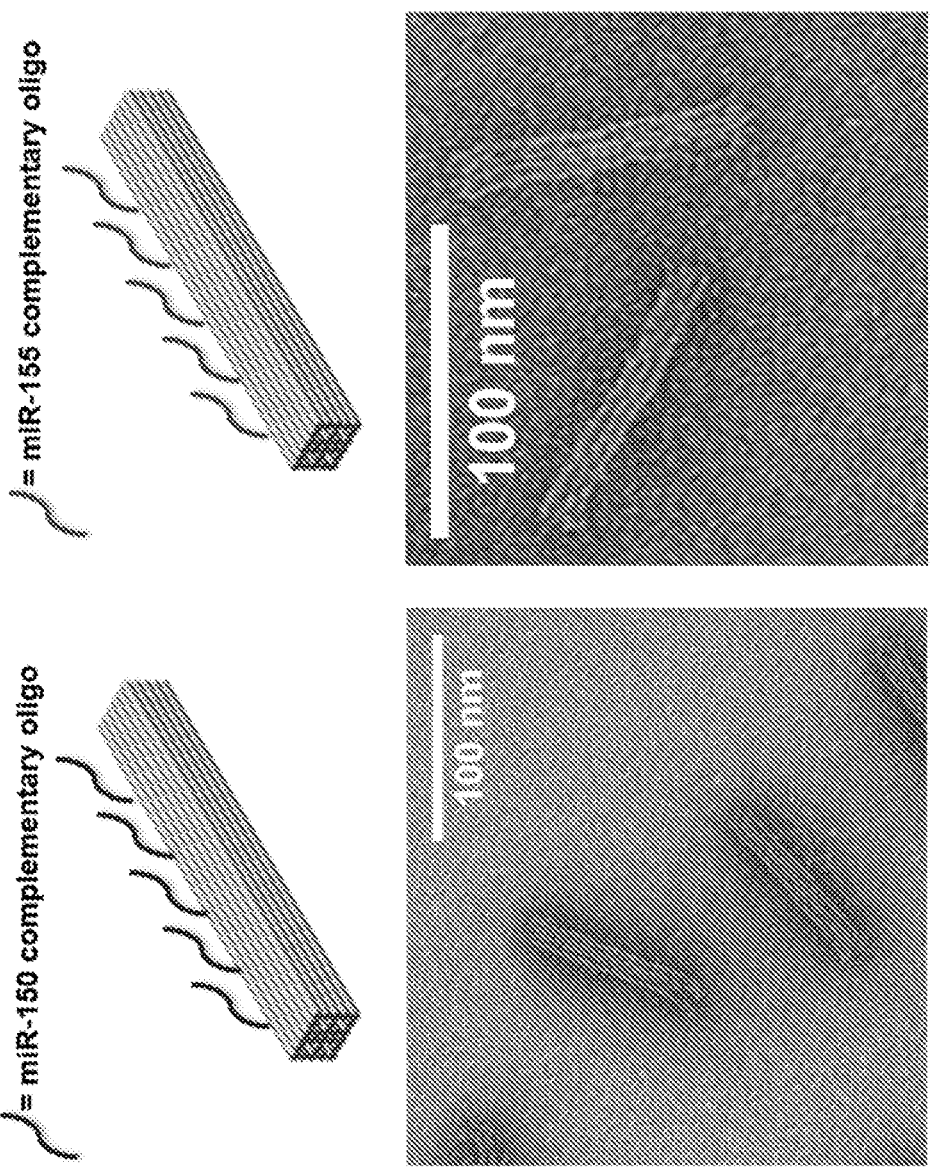
FIG. 4. Schematics and images of drug-loaded delivery devices functionalized with miR-150 (left) and a miR-155 (right) complementary oligonucleotides. Scale bars, 100 nm.

FIG. 4. Schematics and images of drug-loaded delivery devices functionalized with miR-150 (left) and a miR-155 (right) complementary oligonucleotides. Scale bars, 100 nm.

Figure 5:
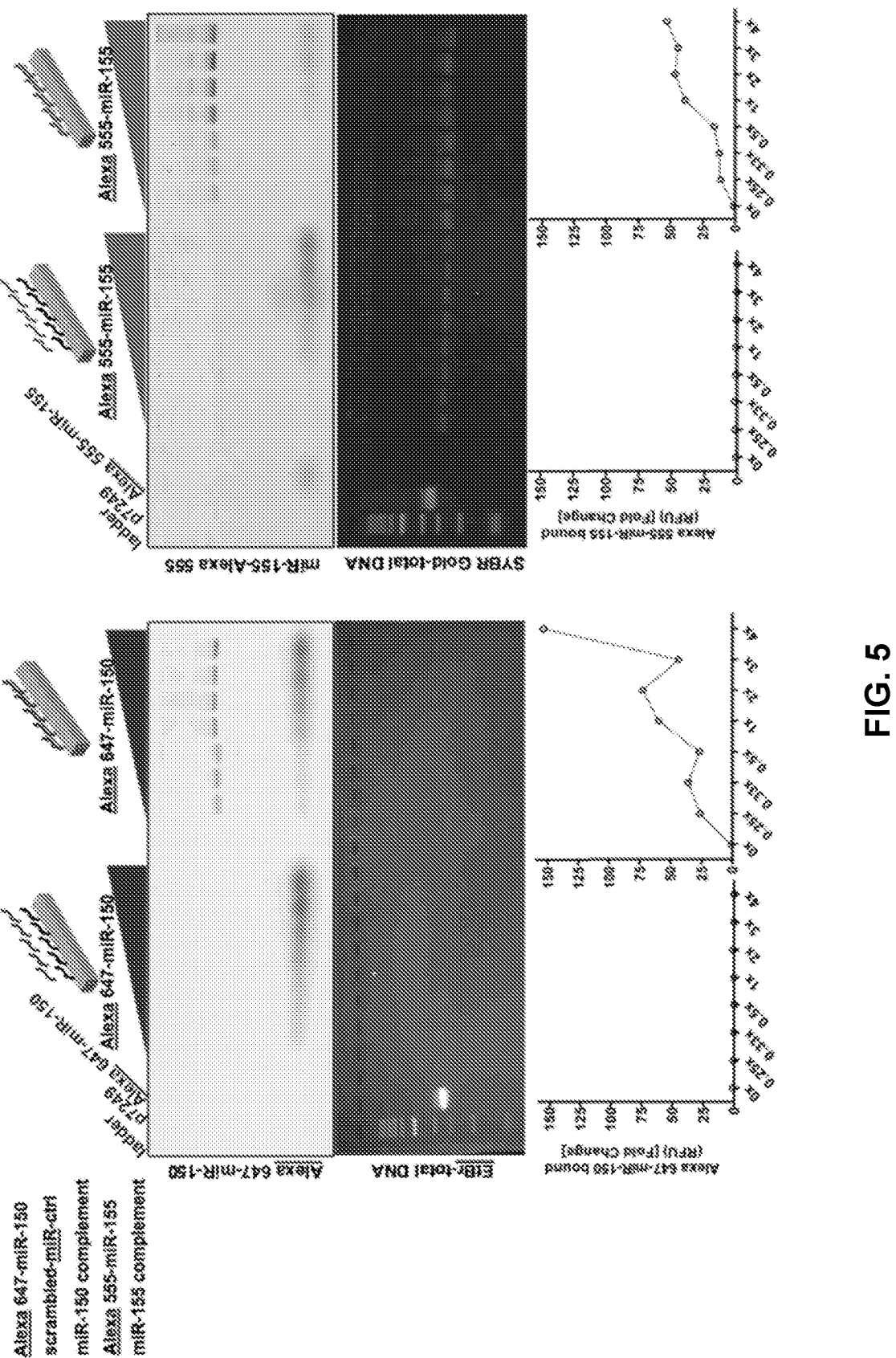
FIG. 5. miRNA binding of delivery devices functionalized with miR-150 (left) and a miR-155 (right) complementary oligonucleotides.

FIG. 5. miRNA binding of delivery devices functionalized with miR-150 (left) and a miR-155 (right) complementary oligonucleotides.

Figure 6:
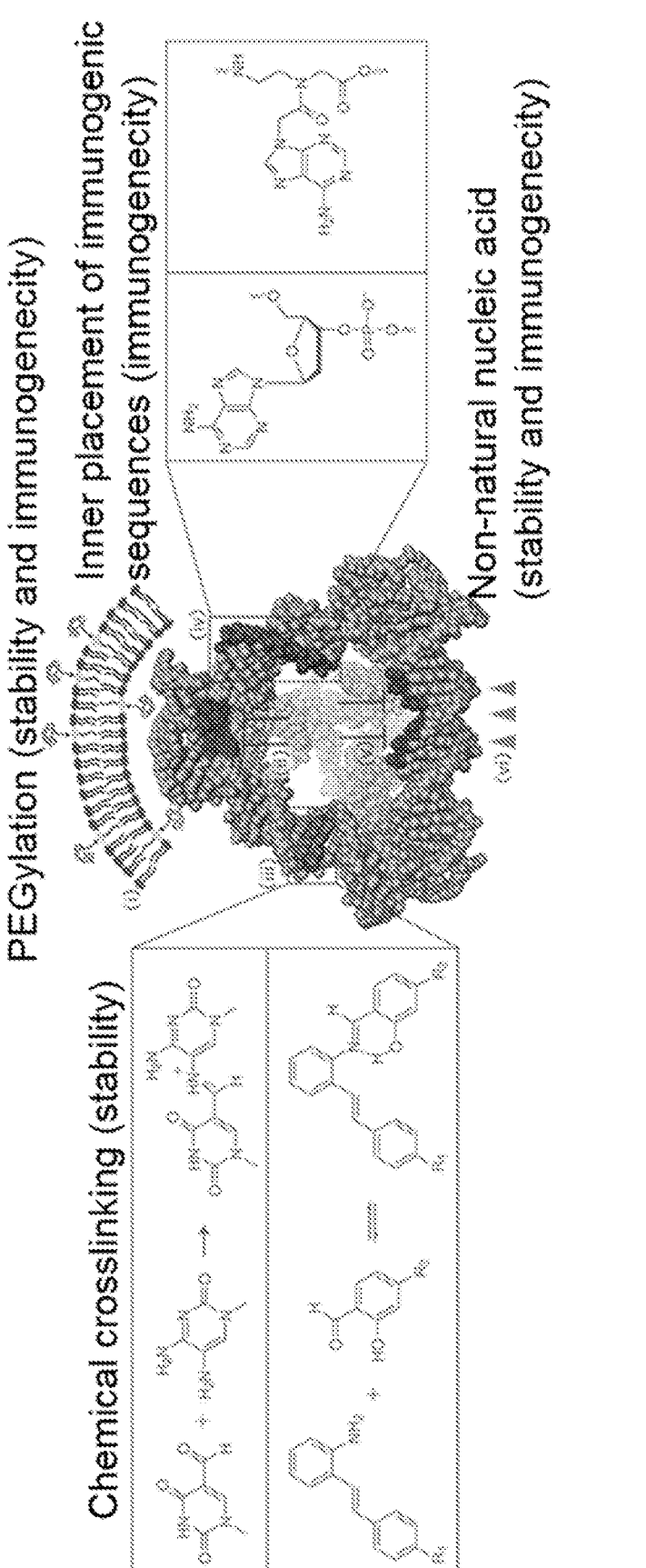
FIG. 6. Illustration of DNA origami challenges.
Figure 9:
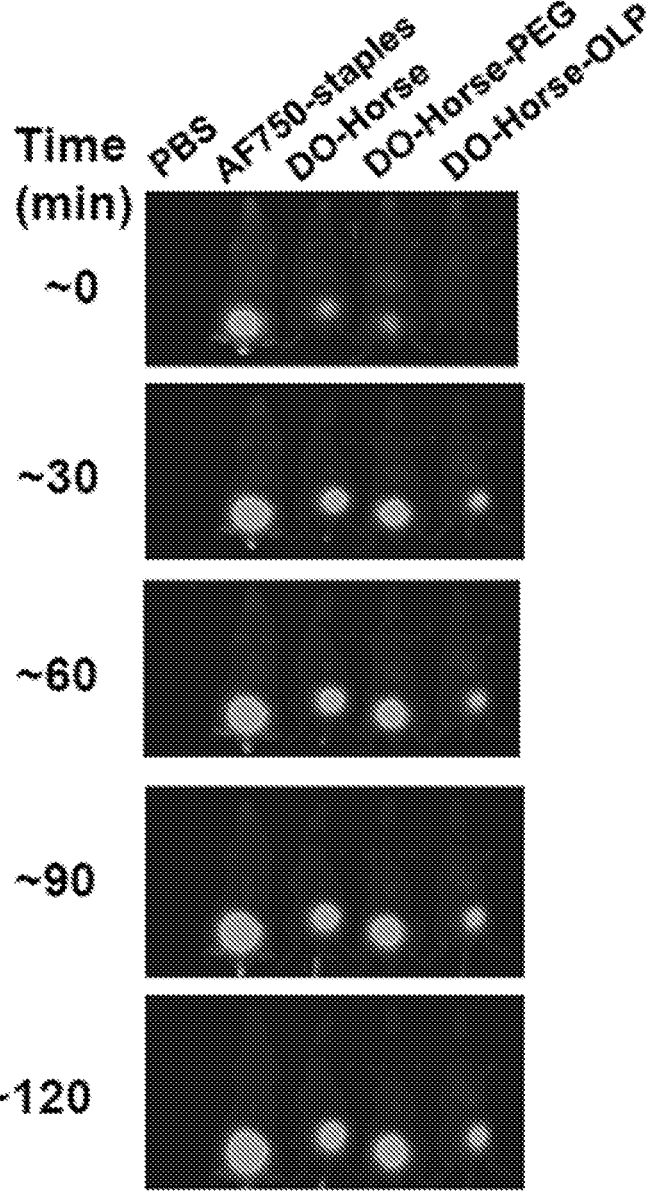
FIG. 9. Pharmacokinetics of Horse-AF750-staples, DO-Horse, DO-Horse-PEG, and DO-Horse-OLP in bladder.
Figure 10:
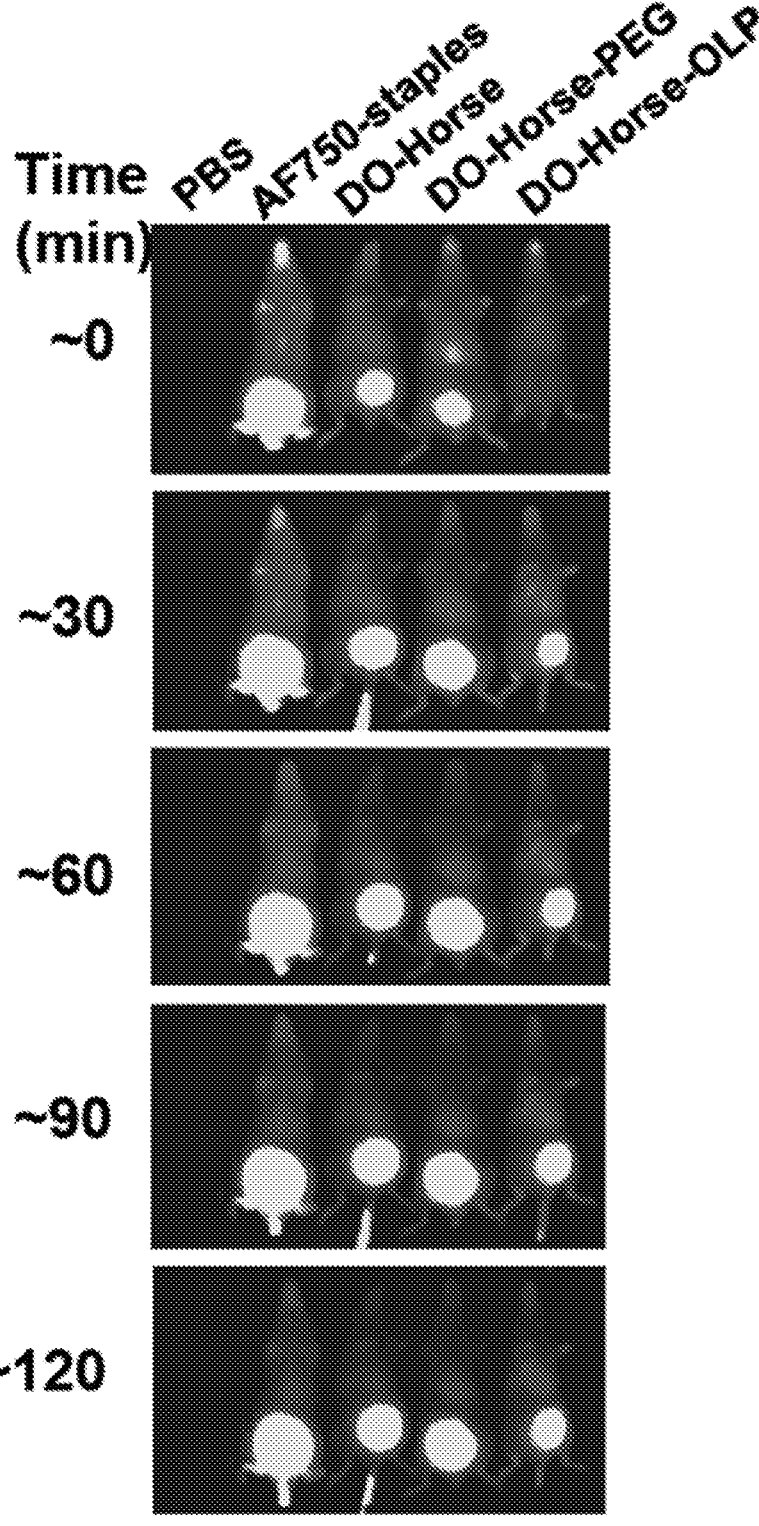
FIG. 10. Pharmacokinetics of Horse-AF750-staples, DO-Horse, DO-Horse-PEG, and DO-Horse-OLP in liver, and periphery.
Figure 11:
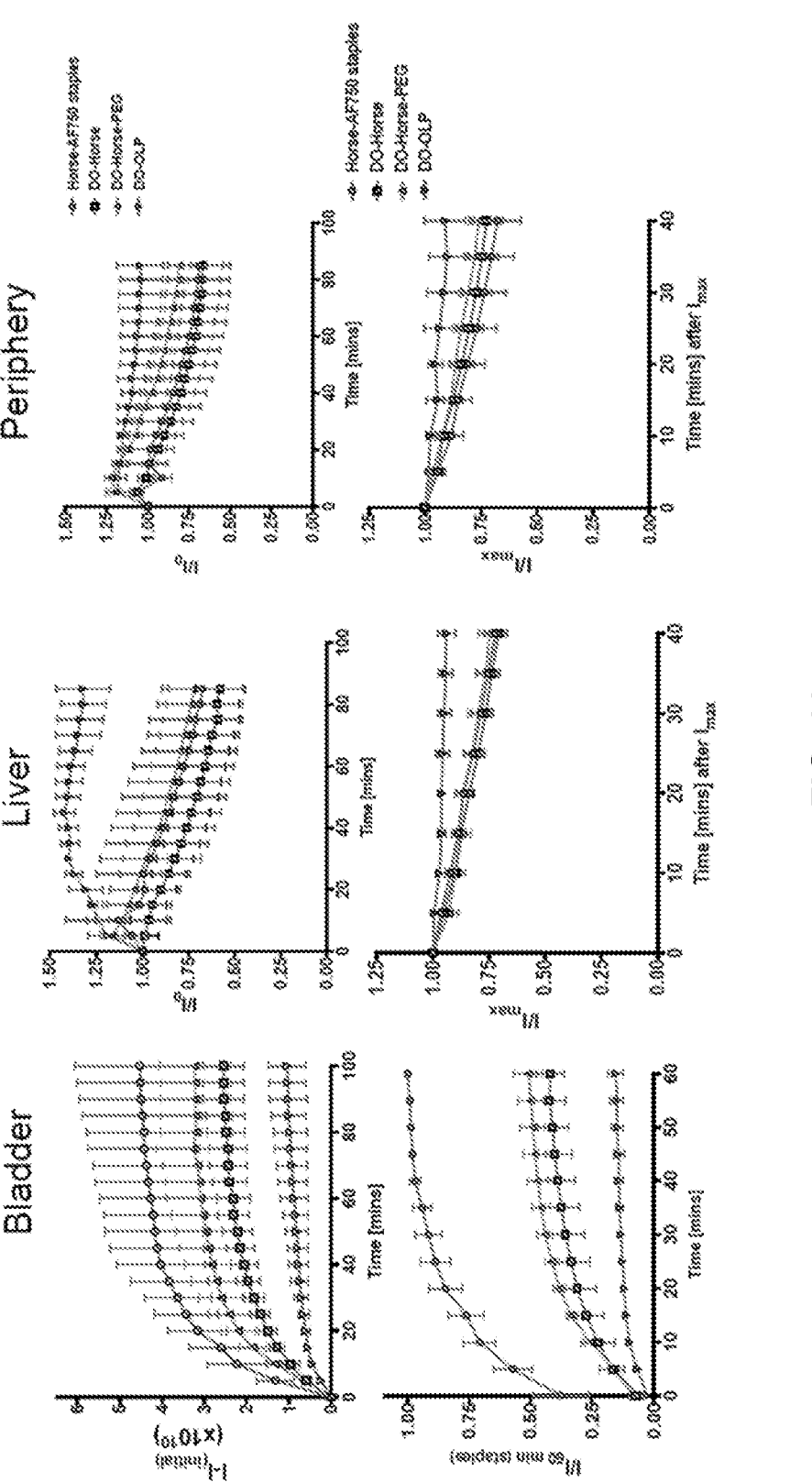
FIG. 11. Pharmacokinetics of Horse-AF750-staples, DO-Horse, DO-Horse-PEG, and DO-Horse-OLP in bladder, liver, and periphery.

FIG. 6. Illustration of DNA origami challenges.

Example 3

The following examples demonstrates improvements to the disclosed DNA origami pharmokinetics using oligolysine polyethylene glycol. FIG. 7 shows schematics of an embodiment modular DNA drug delivery device using either PEGylated oligos (DO-Horse-PEG, left) or PEG molecules attached to lysine residues and attaching to the device by electrostratic interactions (DO-Horse-OLP, right). The DO-Horse-PEG tested contained 65 PEGylated oligos attached to the DNA origami (DO) by complementary oligos embedded in the DO. Using this approach, there is incomplete coverage, and oligos are subjectd to nuclease degradation.

The DO-Horse-OLP embodiment tested involved a PEG molecule attached to 10 Lys residues. This was attached to the DO by electrostatic interactions (10 Lys to anionic DNA backbone). This created a shell of PEG around each exposed helix with approximately 1,450 PEG molecules per DO structure.

FIGS. 8 to 11 demonstrate the improved pharmacokinetics using this approach.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A drug delivery device, comprising a DNA origami nanostructure formed from a plurality of DNA scaffold strands and a plurality of DNA staple strands assembled into a rod shape comprising parallel helices and open cavities that extend along the length of the nanostructure, wherein a small molecule drug is attached to the DNA of the nanostructure, wherein the nanostructure is conjugated to a plurality of polyethylene glycol (PEG) molecules, and wherein at least one targeting antibody that selectively binds a tissue or cell antigen is conjugated to an end of the nanostructure.

2. The device of claim 1, wherein the small molecule drug is an anthracycline.

3. The device of claim 2, wherein the anthracycline comprises doxorubicin, daunorubicin, or idarubicin.

4. The device of claim 1, wherein the targeting agent is an antibody that selectively binds a tumor antigen.

5. The device of claim 1, wherein the PEG molecules are attached to cationic amino acids.

6. The device of claim 5, wherein the PEG molecules are attached to 2, 3, 4, 5, 6, 7, 8, 9, 10, or more lysine residues.

7. The device of claim 1, wherein the nanostructure is conjugated to a plurality of oligonucleotides.

8. The device of claim 1, wherein the parallel scaffold stands are 5,000 to 10,000 bases in length.

9. The device of claim 1, wherein the nanostructure has a quadrilateral cross-section.

10. The device of claim 1, comprising at least 24 parallel helices and four open cavities.

11. The device of claim 7, wherein at least some of the plurality of oligonucleotides are therapeutic antisense RNA, miRNA, shRNA, RNAi, or siRNA.

12. The device of claim 7, wherein at least some of the plurality of oligonucleotides are attached to polyethylene glycol (PEG) molecules.

13. A method for targeted delivery of a drug to a tissue or cell of a subject, comprising administering to the subject the device of claim 1.

14. The method of claim 13, wherein the subject has cancer, wherein the drug is an anthracycline, and wherein the targeting agent is an antibody that selectively binds a tumor antigen.

* * * * *